(12) United States Patent
Hjertman (10) Patent No.: US 7,104,971 B2
(45) Date of Patent: *Sep. 12, 2006

(54) MEDICAL DEVICE

(75) Inventor: Birger Hjertman, Vällingby (SE)

(73) Assignee: Pharmacia AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/353,301

(22) Filed: Feb. 14, 2006

(65) Prior Publication Data

US 2006/0184118 A1 Aug. 17, 2006

Related U.S. Application Data

(60) Division of application No. 10/850,279, filed on May 20, 2004, now Pat. No. 7,033,337, which is a continuation of application No. 09/862,563, filed on May 22, 2001, now Pat. No. 6,740,062.

(60) Provisional application No. 60/209,049, filed on Jun. 2, 2000.

(30) Foreign Application Priority Data

May 22, 2000 (SE) .................................. 001894

(51) Int. Cl.
*A61M 5/00* (2006.01)

(52) U.S. Cl. .................. 604/187; 604/131; 604/191; 604/68; 604/82

(58) Field of Classification Search ............ 604/187, 604/131, 191, 68, 70, 133, 181, 90
See application file for complete search history.

(56) References Cited

U.S. PATENT DOCUMENTS 2,591,046 A 4/1952 Brown
2,821,981 A 2/1958 Ziherl et al.
3,138,257 A 6/1964 Anderson
4,447,225 A 5/1984 Taff et al.
5,472,422 A 12/1995 Ljungquist
5,501,673 A 3/1996 Hjertman et al.
5,605,542 A 2/1997 Tanaka et al.
5,716,338 A 2/1998 Hjertman et al.
5,716,339 A 2/1998 Tanaka et al.

(Continued)

FOREIGN PATENT DOCUMENTS

TW 286287 9/1996

(Continued)

*Primary Examiner*—Henry Bennett
*Assistant Examiner*—Camtu Nguyen
(74) *Attorney, Agent, or Firm*—Dinsmore & Shohl LLP (57) ABSTRACT

The invention relates to an injector device for delivery of liquid from a high pressure source, and also to a method of performing such an injection. The device comprises a storage chamber 6, for the liquid or the liquid precursor components, comprising a storage barrel 16 with at least a section of substantially constant cross-section, defining a storage chamber axis, and a pressure chamber 4 comprising a pressure barrel 10 of substantially constant cross-section, defining a pressure chamber axis, for accommodation of at least one piston therein and having a front end opening 14 for ejection of the liquid. The pressure chamber being of sufficient strength to sustain the liquid pressure. The chambers are separate parts and adapted to cooperate with each other during injection so that the pressure chamber axis and the storage chamber axis substantially coincide, and that the pressure barrel and storage barrel have internal diameters sufficiently similar to allow passage of a resilient piston from the storage barrel to the pressure barrel in a sealing manner. The liquid is transferred from the storage chamber directly into the delivery chamber when the jet injection is to be performed.

6 Claims, 4 Drawing Sheets

U.S. PATENT DOCUMENTS

| | | |
|---|---|---|
| 5,743,890 A | 4/1998 | Hjertman et al. |
| 5,785,682 A | 7/1998 | Grabenkort |
| 5,788,670 A | 8/1998 | Reinhard et al. |
| 5,814,022 A | 9/1998 | Antanavich et al. |
| 5,817,055 A | 10/1998 | Ljungquist |
| 5,817,056 A | 10/1998 | Tanaka et al. |
| 5,840,061 A | 11/1998 | Menne et al. |
| 5,865,799 A | 2/1999 | Tanaka et al. |
| 5,868,713 A | 2/1999 | Klippenstein |
| 5,879,336 A | 3/1999 | Brinon |
| 5,935,101 A | 8/1999 | Kato et al. |
| 6,027,481 A | 2/2000 | Barrelle et al. |
| 6,053,894 A | 4/2000 | Shadd, Jr. |
| 6,077,252 A | 6/2000 | Siegel |
| 6,149,628 A | 11/2000 | Szapiro et al. |
| 6,319,225 B1 | 11/2001 | Sugita et al. |
| 6,406,455 B1 | 6/2002 | Willis et al. |
| 6,740,062 B1 | 5/2004 | Hjertman |

FOREIGN PATENT DOCUMENTS

| | | |
|---|---|---|
| WO | WO 9201485 | 2/1992 |
| WO | WO 9831409 | 7/1998 |

MEDICAL DEVICE

RELATED APPLICATIONS

The present application is a divisional of application Ser. No. 10/850,279 filed May 20, 2004, now U.S. Pat. No. 7,033,337 which is a continuation of application Ser. No. 09/862,563 filed May 22, 2001, now U.S. Pat. No. 6,740,062, which claims priority under 35 U.S.C. § 119 of U.S. application Ser. No. 60/209,049 filed Jun. 2, 2000.

FIELD OF THE INVENTION

The present invention relates to an injector device, a pressure chamber and a method to perform the injection, according to the preambles of the independent claims.

BACKGROUND OF THE INVENTION

The principles of the present invention can be used in connection with any injector requiring high level pressurization of the fluid to be injected. High pressures may be needed for expelling high viscosity product, such as products in oil, gelled, paste, amorphous or suspension form, e.g. for dental purposes or to form slow release deposits in the body. Another major injector type requiring high pressure is jet injectors for needle-less skin penetration of a pressurized liquid to be further discussed below. Although for convenience the invention will be described in terms of such jet injection, the invention shall not be regarded as restricted thereto but shall be understood to embrace other high pressure applications as well.

Jet injection apparatuses for hypodermic jet injection of medical liquids through the skin surface or the mucous membrane of either humans or animals under sufficiently high pressure to force the liquids to a predetermined depth within the tissue beneath the skin surface are known in the art since many years.

A multi-shot injector instrument employing the jet injection principle is known from U.S. Pat. No. 2,821,981. In this known instrument the fluid to be injected is charged into a distal pressure chamber, an ampoule, from a proximal fluid medicine chamber, e.g. in the form of a conventional syringe. One mechanism is used to transfer the fluid from the fluid chamber into the pressure chamber and another mechanism is then used to perform the injection. Non return valves are provided in the transfer bore to ensure that no back flow occurs. The mechanically rather complicated structure of the injector instrument makes it rather expensive to manufacture. Another drawback with this type of complicated mechanical instruments is the difficulty to assemble the device in a sterile environment. It is sometimes today a demand to make parts non-reusable (disposable) that might be contaminated during injection. This demand is very difficult to fulfil for a device of the type disclosed in U.S. Pat. No. 2,821,981, or generally for mechanically complicated devices of this kind, due to the large number of different parts making up the device.

U.S. Pat. No. 3,138,257 discloses an injector device similar to the one of U.S. Pat. No. 2,821,981.

U.S. Pat. No. 4,447,225 discloses a multi-dose jet injector adapted to receive a medicament bottle or vial from which the medicament liquid is transferred into a transfer chamber. The medicament is then pumped through a one-way valve via a cannula to a medicament delivery chamber. The medicament is then ready for jet injection delivery, which is performed by imparting an ejecting force on the medicament liquid and thus expelling it through an orifice of the jet injector. One drawback with the jet injector disclosed in U.S. Pat. No. 4,447,225 is that it is structurally complicated, e.g. the two step transfer of the medicament liquid prior injection, and thus expensive to manufacture.

WO-92/01485 discloses a two-compartment syringe with a barrel, made e.g. from plastic, comprising a distal and a proximal section. An insert made from a material, e.g. glass, which is compatible with the solvent, or liquid medicament, is inserted, into the proximal section of the barrel. The solvent is transferred into the distal section, where the liquid solves a lyophilized powder, via a by-pass arrangement and the syringe is then ready to be used for an ordinary hypodermic needle injection. It should be observed that the syringe disclosed in WO-92/01485 is intended for traditional needle injection, i.e. there is no indications at all that the distal section could resist a higher pressure needed for high pressure injections, e.g. having front sealings and arrangements unable to sustain high pressures. The design is purely adapted for a lyophilisation step to take place in the front compartment.

U.S. Pat. No. 2,591,046 discloses a hypodermic syringe assembly with two chambers separated by a by-pass section. The liquid medicine is transferred into a distal chamber via the by-pass section. There are no separate chambers able to provide different properties, e.g. resistance against high pressures.

Liquid medicaments intended for injection are ordinarily stored in glass containers prior loaded into a syringe for injection. A rubber seal then seals the glass container. Thus, the liquid medicament is only in direct contact with glass and rubber. The major reason for not using plastic materials as material for medical storage containers is that the plastic material does not provide an entirely closed sealing with regard to oxygen moving into or components out from the container. Also components from the manufacture might be deposed in the plastic material that can affect liquid stored in the container. Another reason is that plastic material may give off trace amounts of components that are unacceptable in injectable preparations. The above mentioned drawbacks regarding plastic material used for medical storage containers are valid only when using plastic containers for normal medical storage times, e.g. up to 2 years. When using plastic materials in e.g. syringes etc. where the liquid medicine only contacts the plastic material when the injection is to be performed the above mention drawbacks can not be identified.

In jet injectors using glass containers, the class container must resist the high pressure used to expel the liquid from the container. The glass container is then preferably manufactured from hardened glass, which renders it expensive. On the contrary, plastic materials can easily provide the necessary properties for a pressure chamber, such as strength and resilience with low shattering risks. Glass materials for storage chambers and plastic materials for pressure chambers are also suitable for disposable single-use components.

The object of the present invention is to achieve an easy to use injector device that is less expensive to manufacture than those known from the prior art. Another object of the present invention is to achieve a device not having the above-mentioned drawbacks regarding the sterile handling of parts of the device. A further object is to offer an injector device suitable to be pre-filled with medical and allowing storage over extended periods of time before injection and wherein all surfaces of the device and its parts being or coming into contact with the medical can be kept sterile during manufacture, storage and use. Still another object of the present invention is to achieve a device provided with sterile parts that inherently cannot be reused in order to prevent unauthorized sterilization and reselling of already used devices that might be dangerous to patients.

SUMMARY OF THE INVENTION

The above-mentioned object is achieved by an injector device, a pressure chamber and a method of performing the injection, according to the characterizing portions of the independent claims.

Preferred embodiments are set forth in the dependent claims.

An easy to use injector device is thus achieved having few movable parts and being easy to manufacture. The injector can be used for any high pressure injector application, can be pre-filled with medical and stored without deterioration of the medical and can be manufactured, stored and used under sterile conditions. The device is also suitable for use as a disposable.

DETAILED DESCRIPTION OF PREFERRED EMBODIMENTS OF THE INVENTION

With references to the accompanying drawings the invention will know be described in greater detail. FIGS. 1A–1E shows a schematic illustration of the injection procedure performed by the injector device according to the invention. The injector device comprises a housing 2 where a pressure chamber 4, a storage chamber 6 and a pressurizing mechanism 8 are arranged.

Figure 3:
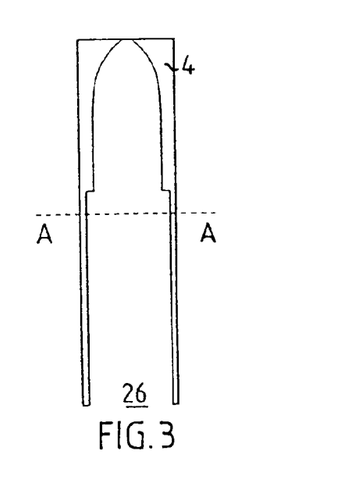
FIG. 3 shows a schematic illustration of a pressure chamber according to the invention.

The pressure chamber, separately shown in FIG. 3, comprises a pressure barrel 10 of substantially constant cross-section, defining a pressure chamber axis 12, for accommodation of at least one piston therein and having a front end opening 14 for ejection of the liquid. The pressure chamber being of sufficient strength to sustain the liquid pressure during the injection procedure. The pressure barrel is provided with an open rear end 26 (in FIG. 3). The pressure chamber is sterilized prior to assembly and is empty or filled with air or a gas. It is preferably disposable but might also be reusable. The inner diameter of the front-end opening is 0,1–0,6 mm, preferably in the order of 0,15 mm. As said, the opening may be adapted either for needle-free jet injection, as schematically illustrated in the Figures, or needle injection, in which case the front opening may have an attachment or connector for a needle. As also known per se a short needle in the range of about 1 to 3 mm can be used to penetrate the outermost part of the skin and thereby reduce the jet speed necessary to reach target depth in the tissue.

The storage chamber 6, for storing the liquid or the liquid precursor components, comprises a storage barrel 16 with at least a section of substantially constant cross-section, defining a storage chamber axis 18, for accommodation of at least one piston 20, 22 therein. A by-pass section is optionally arranged therein (not shown in the figure). The storage barrel is provided with an open front end and preferably an open rear end. Most preferably the storage chamber has a substantially constant cross-section from front end to rear end to give the generally cylindrical shape shown. The inner cross-section area of the storage barrel should be adapted to the inner cross-section area of the pressure barrel so as to allow passage of a sealing piston from the storage barrel to the pressure barrel, e.g. by the storage barrel being smaller and preferably equal to the pressure barrel and preferably the cross-section areas and shapes are substantially similar. A front sealing piston (22) is arranged in the open front end and another rear sealing piston (20) is arranged in the rear end of the storage barrel.

Figure 2:
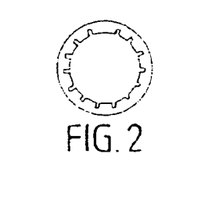
FIG. 2 shows a cross-sectional view along the line A—A in FIG. 3.

A liquid connection 24 is arranged between the pressure chamber and the storage chamber allowing transfer of the liquid from the storage chamber to the pressure chamber. In the figure the liquid connection is a conventional by-pass section in the pressure chamber. FIG. 2 shows a cross-sectional view along the line A—A in FIG. 3 (that schematically shows the pressure chamber) illustrating a preferred embodiment of the by-pass section.

The illustrated by-pass section comprises one or many traces, by-pass channels, on the inner surface of the by-pass section of the pressure chamber. The by-pass channels can be parallel to the longitudinal direction of the delivery chamber, e.g. as described in U.S. Pat. No. 5,501,673. They could also being arranged in an angle to the longitudinal direction, e.g. as described in U.S. Pat. No. 5,716,338. The number of channels is chosen in dependence of the amount of liquid to be transferred, preferably in the order of 1–15. The by-pass section may be arranged in many different ways. It may be arranged at the inner surface of the pressure chamber as illustrated in the figures. It may also be arranged at the inner surface of the upper part of the storage chamber giving an equivalent by-pass function. Many further different ways to arrange the by-pass section are known from the prior art.

It is important that not too many channels are arranged due to the volume of liquid that remains in the channels when the liquid is transferred. It is also suitable to reduce the dead volume held between any circumferential ridges on the pistons by keeping the difference small between the diameter through the ridges and through the main body of the piston respectively.

According to an alternative embodiment is the shape of the inner surface of the by pass section such that the piston is deformed when passing the section and thereby allows liquid to pass from the storage chamber into the pressure chamber e.g. as described in U.S. Pat. No. 5,472,422 and U.S. Pat. No. 5,817,055.

The storage chamber is separate from the pressure chamber and preferably made from different material. According to a preferred embodiment is the storage chamber made from glass, e.g. Type I glass, and the pressure chamber made from plastic, e.g. polycarbonate. The chambers are assembled together by inserting the storage chamber into the pressure chamber. A sealing 30, preferably an O-ring, is arranged between the chambers in order to achieve a fluid-tight connection to the pressure barrel to avoid backflow and to maintain sterility. Also the front opening can have a temporary seal to maintain the pressure chamber sealed and sterile, e.g. a seal in the form of a closure or a rupturable or removable membrane. Assembling the chambers is performed in a sterile environment, e.g. as an additional step on the production line where the storage chamber is filled with liquid medicine. When assembled, the pressure chamber axis and the storage chamber axis substantially coincide.

The assembly is then arranged in the housing 2 provided with the mechanism 8 when the injection is to be given. This does not have to be made in a sterile environment. The assembly of the pressure chamber and the storage chamber is preferably disposed after use but the housing and the pressurizing mechanism might be used many times.

The pressure barrel and storage barrel have internal diameters sufficiently similar to allow passage of a resilient piston from the storage barrel to the pressure barrel in a sealing manner, except when in the optional by-pass or the liquid connection section. The pressurizing mechanism arranged to apply force (indicated by an arrow in the figures), directly or indirectly, on the piston, via plunger 28, when in the pressure barrel to create said liquid pressure necessary for injection. The mechanism is only schematically indicated in the figures and may be e.g. spring loaded as disclosed in U.S. Pat. No. 4,447,225. According to another principle is the injecting force generated by gas under pressure. These two principles are well known in the art. The pressure inside the pressure chamber during injection is in the order of 4000 psi (Pounds per square inch).

The pistons of the storage chamber are used, not only to seal the storage chamber, but also when transferring the liquid into the pressure chamber.

The different steps performed during an injection procedure will now be described with references to FIGS. 1A–1E.

The different steps performed is basically a three step procedure comprising a transfer step where the liquid is transferred from the storage chamber into the pressure chamber, a step for removing air from the pressure chamber and an injection step. The liquid transfer and the de-aeration steps are preferably performed fairly slowly and under low pressure, not to induce glass breakage, plunger overshooting in the by-pass, liquid foaming or liquid spraying through the opening. Only the injection step has to be performed under high pressure. The simple design of the device according to the invention allows all steps to be performed by a forward movement of the support 28, as illustrated in the Figures, although the speed and force requirements may vary. As will be further commented on below, it is also possible to use different mechanisms for the different steps, each adapted for its purpose.

Figure 1A:
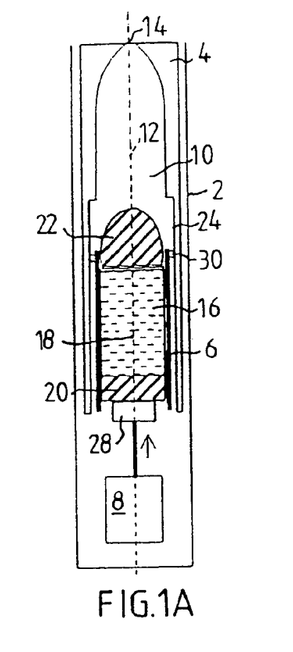
FIGS. 1A–1E show a schematic illustration of the injection procedure performed by the injector device according to the invention.
Figure 1B:
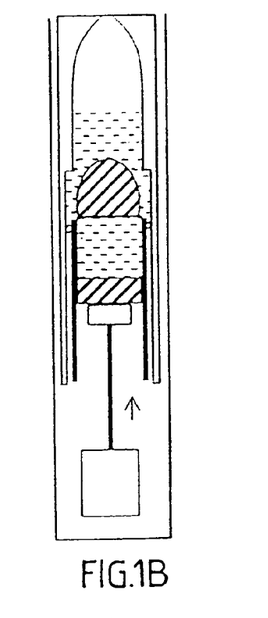

During the transfer step the rear piston of the storage chamber is forced by the pressurizing mechanism in an upward direction (FIG. 1A). Due to the pressure from the rear piston 20 the liquid forces the front piston 22 into the by-pass section where liquid by-pass the front piston 22 into the pressure chamber (FIG. 1B). This first step is ended when all liquid is transferred into the pressure chamber, i.e. the pistons 20,22 are in close contact to each other. The surfaces of the pistons facing each other preferably have such a shape that when they are in contact with each other no liquid remains between the pistons. They preferably have flat surfaces engaging each in order not to be resilient when under pressure. This can be obtained by designing the surfaces with slightly convex shape under unstressed conditions, to become flat under radial compression, as described in U.S. Pat. No. 5,743,890.

The pressure on the rear piston, during the transfer step, is illustrated in the figure as a force generated by the pressurizing mechanism. This illustrates only the relative pressure/movement between the plunger 28 and the piston. According to another and preferred embodiment is the pressure during the transfer step achieved by instead moving the pressure chamber and storage chamber assembly on one hand and the plunger 28 and mechanism 8 assembly on the other hand relatively towards each other, under which operation the plunger 28 and mechanism 8 preferably are kept mutually stationary. This can be done by arranging the respective assemblies in different housing parts, which parts are movable in relation to each otherplunger e.g. by a relative rotate screwing movement of the two parts of the housing, e.g. as described in U.S. Pat. No. 4,968,299, which will secure a calm and cautious liquid transfer. The liquid is forced into the pressure chamber from the storage chamber and no non-return valves are needed. Preferably also de-aeration is performed during such a relative movement between the parts. This arrangement also has the advantage of reducing the requirements on the mechanism 8, which can now be designed only for the injection step, e.g. by comprising a strong gas spring or mechanical spring and a trigger mechanism for its release. Such mechanisms are well known in the jet injection art as exemplified by the prior art cited.

Figure 1C:
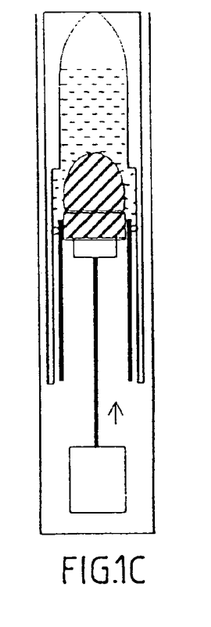
Figure 1D:
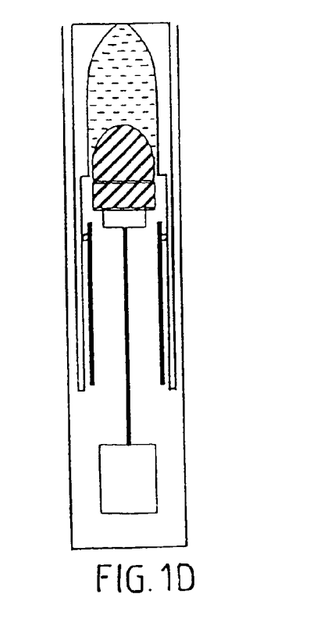

During the air removing step both pistons are forced into the by-pass section and further into the pressure chamber (FIG. 1C). How far the pistons are inserted into the pressure chamber is dependent of the volume of liquid transferred into the chamber. It is important that there is no air in the pressure chamber when the injection is performed. The pistons provide a tight sealing of the pressure chamber. FIG. 1D illustrates the situation when the air removing step is concluded i.e. no air is left in the pressure chamber. Moving the pistons during this step may either be performed by moving the housing or a part of the housing against the plunger 28, i.e. in the same way as in the transfer step, or by activating the mechanism 8.

Both during the transfer step and during the air removing step the device is preferably held in a somewhat upright position, i.e. the front end opening of the pressure chamber above horizontal, aslant or substantially facing upwards, in order to prevent the liquid to pour out.

Figure 1E:
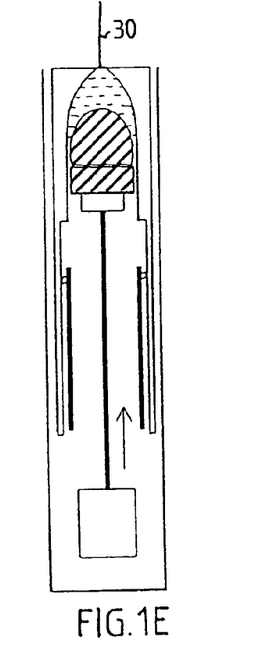

The injector device is now ready for injection (FIG. 1D). The pressurizing mechanism 8 engaging the pistons via plunger 28 is activated and a necessary force is applied on the pistons in order to propel a liquid jet 30 from the front end opening 14 of the pressure chamber (FIG. 1E). The upper end of the pressure chamber is held in tight connection against the skin of a patient when the injection is performed.

The distal part of the front piston 22 is preferably adapted to fill out the pressure chamber front end when the plunger reaches that end. This is important in order to expel as much liquid as possible from the pressure chamber during the injection.

According to an alternative embodiment is the storage chamber divided, by a third piston and provided with a by-pass section, into two separate compartments whereas the proximal compartment comprises a liquid, e.g. water, and the distal compartment comprises a solid component, e.g. a lyophilized powder. The liquid is forced into the distal compartment via the by-pass section where a liquid solves the solid component. This is a well-known procedure in the art of two compartment syringes. The thus mixed liquid located in the distal compartment is then transferred into the pressure chamber in exactly the same manner as described above.

FIGS. 4A–4D shows a schematic illustration of the injection procedure performed by the injector device according to the alternative embodiment of the invention.

In FIGS. 4A–4D only the pressure chamber 4 and the storage chamber 6 and the pistons and sealing within these chambers are illustrated. The pressure and storage chamber assembly is of course arranged within a housing having all necessary features to perform an injection in accordance with the embodiments disclosed above.

The pressure chamber 4 comprises a pressure barrel 10 of substantially constant cross-section for accommodation of at least one piston therein and having a front end opening 14 for ejection of the liquid. The pressure chamber being of sufficient strength to sustain the liquid pressure during the injection procedure. The pressure barrel is provided with an open rear end 26 (in FIG. 3).

The pressure chamber is sterilized prior use and is filled with air or a gas. It is preferably disposable but might also be reusable.

The inner diameter of the front-end opening is 0,1–0,6 mm, preferably in the order of 0,15 mm.

The storage chamber 6, for storing the liquid or the liquid precursor components, comprises a storage barrel 16 with at least a section of substantially constant cross-section for accommodation of a first, or rear, piston 20, a second, or front, piston 22 and a third, or intermediate, piston 23 therein.

A by-pass section 25 is arranged therein.

A liquid connection 24 is arranged between the pressure chamber and the storage chamber allowing transfer of the liquid from the storage chamber to the pressure chamber. The liquid connection may be a conventional by-pass section in the pressure chamber.

The chambers are assembled together by inserting the storage chamber into the pressure chamber. A sealing 30, preferably an O-ring, is arranged between the chambers in order to achieve a fluid-tight connection to the pressure barrel. Assembling the chambers is performed in a sterile environment, e.g. as an additional step on the production line where the storage chamber is filled with liquid and a solid component.

The different steps performed during an injection procedure will know be described with references to FIGS. 4A–4D.

The different steps performed is similar to the three step procedure described in connection with FIGS. 1A–1E, i.e. comprising a transfer step where the liquid is transferred from the storage chamber into the pressure chamber, a step for removing air from the pressure chamber and an injection step. In this embodiment a preparing step is added before the transfer step.

The storage chamber comprises two compartments separated by a sealing, intermediate, piston 23. The lower compartment 31 contains a liquid, e.g. water, adapted to solve a solid component 35, e.g. a lyophilized powder, in the upper compartment 33.

Figure 4A:
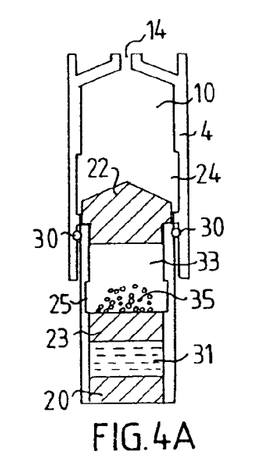
FIGS. 4A–4D show a schematic illustration of the injection procedure performed by the injector device according to a second preferred embodiment of the invention.
Figure 4B:
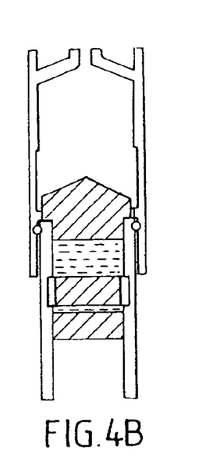
Figure 4C:
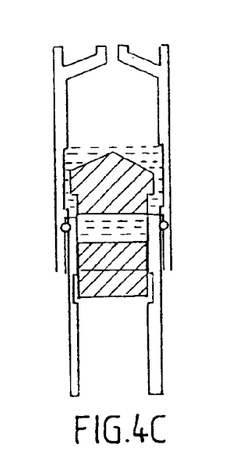

During the preparing step (FIGS. 4A, 4B) the first piston 20 is forced (e.g. by the pressurizing mechanism or as alternatively described above) in an upward direction and forces via the liquid in the lower compartment 31 the third piston into the by-pass section 25. When the liquid enters the upper compartment 33 via the by-pass section it dissolves the solid component. When all liquid is transferred into the upper compartment 33 and the solid material is solved the first and third pistons together continue upward forcing via the liquid the second piston 22 into the by-pass section 24 of the pressure chamber. When in that position liquid is transferred (transfer step of the procedure) into the pressure chamber (FIG. 4C).

Figure 4D:
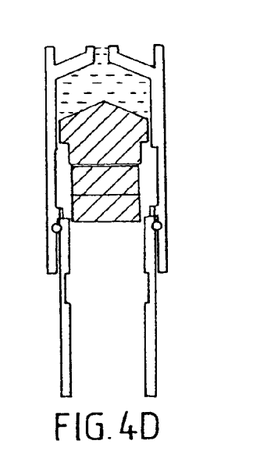

FIG. 4D illustrates the injector device ready for injection in that the second piston 22 is forced out from the by-pass section and is in a fluid tight sealing against the inner surface of the distal part of the pressure chamber. The exact position of the piston within the pressure chamber when the device is ready for injection depends of the volume of the liquid transferred into the pressure chamber. In that position substantially all air is expelled from the pressure chamber through the front end opening 14.

In the embodiment of FIGS. 4A to 4D the internal diameter of the pressure barrel is slightly larger than the internal diameter of the storage barrel and the second piston 22 has a larger diameter upper or front part, adapted to the diameter of the pressure chamber, and a smaller lower or rear part, adapted to the diameter of the storage barrel, enabling it to seal against both chambers. The smaller first piston 20 and third piston 23 can continue their movement into the pressure barrel while the second piston provide sealing therein.

Figure 5:
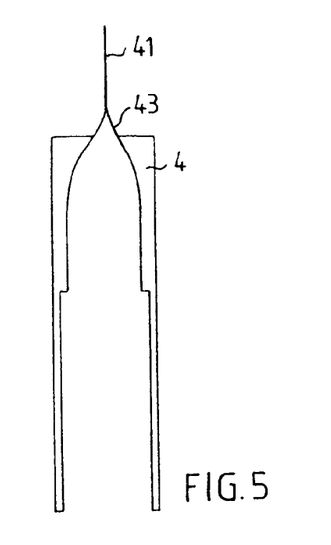
FIG. 5 shows a schematic illustration of the pressure chamber according to an alternative embodiment of the invention.

Throughout the description of the present invention the high pressure jet generated by the device is arranged to penetrate the skin of a patient. However the basic principles of the invention is equally applicable when performing needle injection of liquid medicines having high viscosity, e.g. gels. If e.g. a gel is to be injected today by a needle syringe a needle having a comparatively large inner diameter must be used which might be very painful. In FIG. 5 a schematic illustration of an alternative embodiment of the pressure chamber according to the invention is shown. In this embodiment a hypodermic needle 41 is attached in connection with the front end opening of the injector device. The connection 43 is performed in a robust manner in order to withstand the pressure inside the pressure chamber during injection. The needle is preferably attached to the pressure chamber during the manufacture of the chamber, e.g. during a molding process. The injection procedure is the same as when performing a needle less jet injection as described above. By using a pressure chamber provided with a needle having a similar inner diameter as the front end opening of the pressure chamber a liquid having a high viscosity can be injected using a thinner needle than before. This is very advantageous in that it is less painful for the patient.

The necessary pressure needed to perform the needle injection according to the alternative embodiment is inter alia dependent of the inner diameter of the needle and the viscosity of the liquid gel.

Typical pressures in the pressure chamber are in general above 25 atm (2,5 MPa), often above 50 atm (5 MPa) or above 100 atm (10 MPa). Normally the pressures are below 1000 atm (100 MPa), often below 800 atm (80 MPa) or below 500 atm (50 MPa).

Figure 6A:
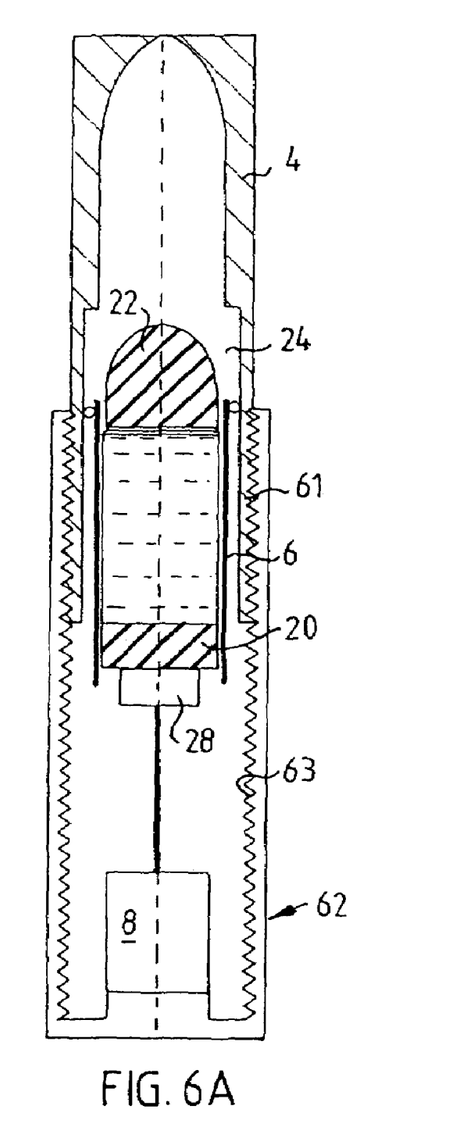
FIGS. 6A–6B show a schematic illustration of an alternative embodiment in which an assembly of pressure chamber and storage chamber is movably arranged with respect to a housing part containing an injection mechanism.
Figure 6B:
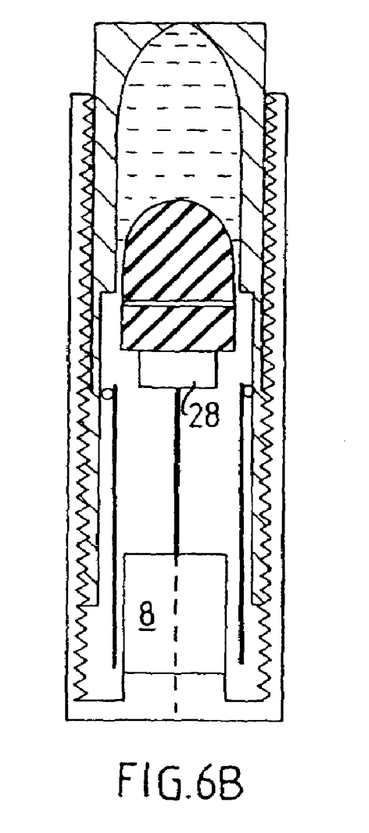

FIGS. 6A–6B show a schematic illustration of an alternative embodiment in which an assembly of pressure chamber and storage chamber is movably arranged with respect to a housing part containing an injection mechanism. As in the other embodiments the pressure chamber 4 and the storage chamber 6 forms an aggregate with the storage chamber inserted coaxial and stationary into the pressure chamber rear end. In this embodiment the pressure chamber rear end is provided with external screw-threads 61. A housing 62 accommodates the mechanism 8 for propelling the plunger 28 forwards and can for example include a spring and a trigger arrangement. The housing 61 has internal screw-threads corresponding to the external threads 61 on the pressure chamber 4. FIG. 6A illustrate the device before any liquid transfer, e.g. as pre-filled and delivered to the end user. The user initiates the device by screwing together the pressure chamber 4 and the housing 62 while the plunger 28 is idle and stationary with respect to the housing. This will cause the rear piston 22 to move forwards to perform the same preparation phases as described for the other embodiments, i.e. displacement of front plunger into the liquid connection 24, transfer of liquid into the pressure chamber and de-aeration of the pressure chamber. The device will now be in the state illustrated in FIG. 6B, where the mechanism 8 and plunger 28 have their initial positions, and is ready for injection. Injection may take place by triggering stored energy in the mechanism 8 to move the plunger 28 forwards under expulsion of the liquid in the pressure chamber 4.

Figure 7A:
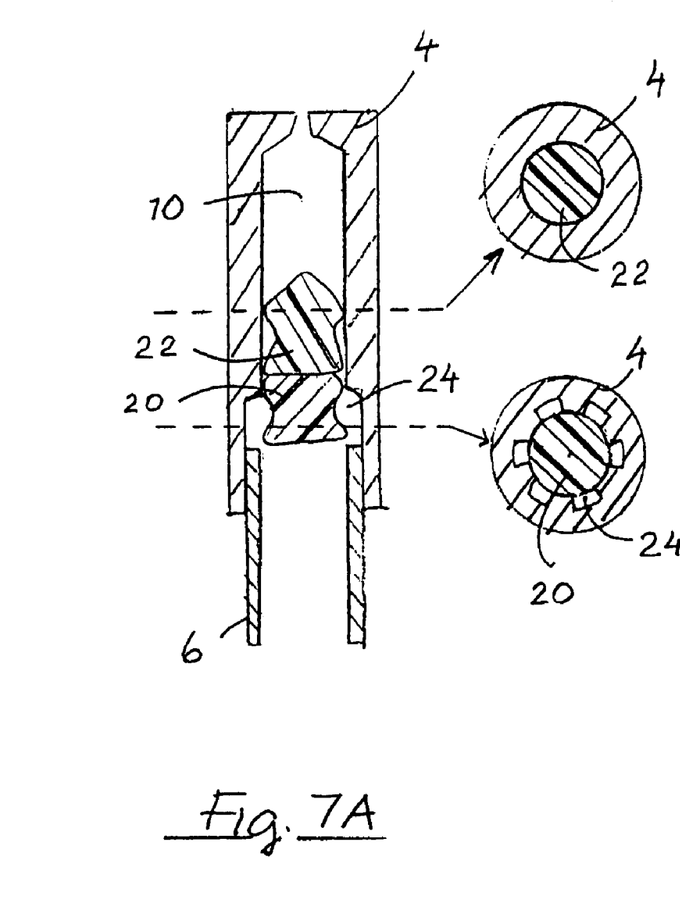
FIGS. 7A and 7B illustrate schematically a plunger arrangement modification for the purpose of reducing the total elasticity in the system.
Figure 7B:
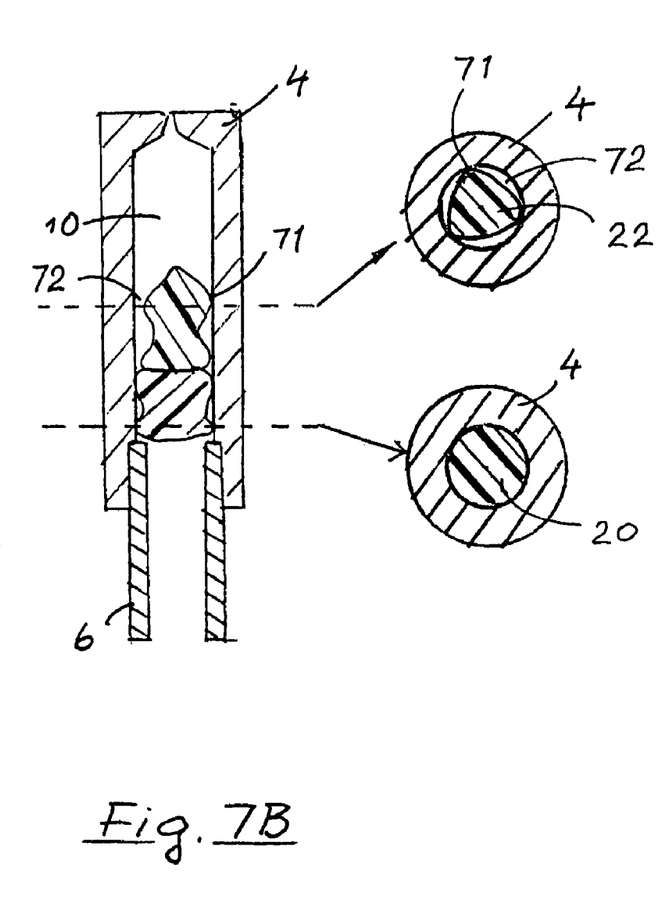

FIGS. 7A and 7B illustrate schematically a plunger arrangement modification for the purpose of reducing the total elasticity in the system during the injection step. FIG. 7A is similar to that illustrated in FIG. 1, i.e. having a pressure chamber 4 and a storage chamber 6, with a liquid connection 24 in between, and front 22 and rear 20 pistons adapted for movement in the chambers. In FIG. 7A the inner diameters of the pressure chamber and the storage chamber are substantially similar, meaning that the pistons have about equal radial compression when in the storage chamber and when in the pressure chamber, which compression certainly shall be sufficient for sealing against the chamber inner walls. Accordingly the pistons are supposed to fill out the inner cross section areas of the chambers, as illustrated in the cross-sections to the right. The upper cross-section is a cut through the pressure chamber 4 barrel part 10 and the front piston 22, when the piston is fully within the barrel and filling out the cross-section, except possibly at plunger parts between plunger sealing ridges. Similarly the lower cross-section is a cut through the pressure chamber 4 at the liquid connection 24 and the rear piston 20, when at this liquid connection, and the piston 20 fills out the cross-section except in the liquid connection channels. It is clear that the pistons are in a position when all liquid has been transferred from the storage chamber to the pressure chamber and both plungers have been mover a bit further forwards, e.g. for de-aeration and ready for injection. When a pressurising mechanism applies force on the rear piston 20, both pistons tend to be deformed since the front piston surface to wall friction resists movement and the deformation can be considerable since the axial force in turn tend to expand the pistons radially. The effect may be exacerbated by the size and the number of pistons, e.g. for dual chamber storage chambers as illustrated in FIG. 4. Elasticity may give rise to ringing and vibration in the pressure profile during injection with arbitrary and less reliable results. FIG. 7B illustrates some modifications to overcome these problems. The storage chamber 6 inner diameter is here slightly less than the inner diameter, at least in the front part of the storage chamber, of the pressure chamber 4, meaning that the radial pressure is reduced on any piston moving from the storage chamber to the pressure chamber. Furthermore the front piston 22 is designed to seal when in the storage chamber but not to seal when in the pressure chamber whereas the rear piston is designed so as to seal both when in the storage chamber and in the pressure chamber. This is illustrated in the cross-sections to the right. As in FIG. 7A the upper cross-section is a cut through the pressure chamber 4 barrel part 10 and the front piston 22, when the piston is fully within the barrel, and it can be seen that the piston has been given a somewhat triangular shape so as to make point contact 71 with the pressure chamber 4 interior wall and leave spaces 72 allowing liquid to pass. In the lower cross-section a cut through the pressure chamber 4 and the rear piston 20 illustrates that this piston fills out the cross-section and seals against the pressure chamber interior wall. In the embodiment shown there is no need for a liquid connection in the form of a by-pass cut-out in the chamber walls since the spaces 72 allow passage of liquid from the storage chamber to the pressure chamber once the front plunger has moved into the pressure chamber and accordingly will act as liquid connection. The eliminated or reduced friction for the front plunger will reduce the deformations in this plunger during injection and accordingly the system overall elasticity. In particular the fact that the pressure in the pressure chamber will have access to all sides of the front piston reduces deformation of this piston.

Other designs than the one illustrated in FIG. 7B can be used for the purposes indicated. The minimum requirement is that the front piston surface to wall friction is reduced in relation to that required for full and safe sealing in the pressure barrel, e.g. by barely contacting the wall or having a small tolerance in between, in which case a by-pass in the barrel wall again may be needed. Preferably the design allows for the pressure to equalise around at least the front piston axial sides, which may require larger spaces than for friction reduction only. Most preferably the piston may leave a larger circumferential gap to the wall, sufficient to allow the liquid to pass and accordingly act as liquid connection although it is preferred to maintain some pressure point contact, e.g. point spacers, or axial line contact, e.g. axial or helical ridges, contact with the wall in order to avoid tumbling or inadvertent displacement towards the barrel front, e.g. by having the non-circular cross-section shown or vice versa, i.e. having a circular piston in a non-circular barrel or a barrel with interior wall ridges. The front piston may have conventional annular ridges although it also possible to reduce or eliminate such ridges in order to facilitate the piston non-sealing properties upon expansion. Any contact surface is less harmful the less its axial extension and the more to the rear its location, e.g. even a trailing annular ridge or skirt would be acceptable. In contrast, a piston intended to seal also after expansion may be given improved properties in this respect e.g. by being sufficiently large, deformable or rilled to fill out also the pressure barrel after expansion. Any such design adaptation need not be extreme, however, since the later applied plunger pressure will make the piston expand somewhat, giving amplified sealing contact. However, the requirement is only that such a piston seals in the pressure chamber. This can be obtained also without expansion in relation to its sealing position in the storage chamber. For example, in the embodiments with equal internal cross-sections for pressure chamber and storage chamber, the storage chamber front and/or the pressure chamber rear can have a constriction, suitable for sealing by a smaller front piston, whereas the requirement on the rear piston is only that it shall be able to pass the constriction and then re-expand, which is facilitated if the constriction is continuous or smooth, at least at the entrance side to the rear.

Any means or designs can be used to reach the intended reduction in piston deformation. As mentioned the pressure chamber interior cross-section area can be larger than the corresponding area in the storage chamber, either with a stepwise change as illustrated or a continuous increase, at least over a rear section of the pressure chamber barrel or a front part of the storage chamber. If the piston has an enlarged portion outside the storage chamber, as illustrated in FIG. 4, the area adaptations should be made with respect to the enlarged portion. Alternatively or in addition the to the area change a barrel cross-section area shape change can be utilised to secure that the piston to barrel shape changes from a high fit in the storage chamber to a less fit in the pressure chamber.

To reach the objects stated the deformation reduction principles outlined should be applied to at least one piston but can be applied to more than one piston, e.g. to the front and intermediate pistons in the FIG. 4 embodiment. In general it is possible to have more than one sealing piston in the pressure barrel although often sufficient to have one sealing piston, preferably the second from front piston to reduce dead volumes. To seal in a reliable and permanent way pistons are normally made of elastically, rather than plastically, deformable material such as rubber. For the purposes outlined it is preferred that the material in the pistons additionally is deformable but non-compressible, e.g. by avoiding gas vesicles or foamed components. Again, it might be of interest also to reduce the dead space present between the common sealing ridges on the pistons or replace them by other adaptive arrangement such as a soft or compressible skin.

The present invention is not limited to the above-described preferred embodiments. Various alternatives, modifications and equivalents may be used. Therefore, the above embodiments should not be taken as limiting the scope of the invention, which is defined by the appendant claims.

The invention claimed is:

1. A pressure chamber and storage chamber combination to be used for jet injection of a liquid medicine, comprising
   (a) a pressure chamber including a pressure barrel of substantially constant cross-section, defining a pressure chamber axis adapted for accommodation of at least one piston therein, and having a front end opening for ejection of the liquid, the pressure chamber being of sufficient strength to sustain the pressure of liquid from a high pressure source, wherein said pressure barrel is provided with an open rear end adapted to receive a storage chamber for the liquid or the liquid precursor components; and
   (b) a storage chamber, including a storage barrel with at least a section of substantially constant cross-section, defining a storage chamber axis, at least one front sealer or piston and at least one rear sealer or piston, the pistons being inserted in the storage barrel and enclosing a liquid or liquid precursor components,
   wherein the pressure chamber and storage chamber are adapted to be interconnected with the pressure chamber axis and the storage chamber axis in substantially co-axial relationship, the pressure barrel and storage barrel have substantially similar internal diameters, and the pressure chamber has a sufficient volume for accommodation of substantially all liquid transferred from the storage chamber.

2. Combination according to claim 1, wherein the pressure chamber is made from plastic.

3. Combination according to claim 1 provided with a liquid connection between the pressure chamber and the storage chamber adapted to allow transfer of the liquid from the storage chamber to the pressure chamber.

4. Combination according to claim 1 wherein the liquid connection comprises a by-pass arrangement on the pressure barrel adapted to allow passage of liquid around the pressure chamber piston.

5. Combination according to claim 1, further comprising an area to the rear of the liquid connection adapted for a seal between the pressure chamber and the storage chamber.

6. Combination according to claim 1, further comprising a hypodermic needle attached in connection with the front end opening to be able to perform a hypodermic injection.

* * * * *